US010675193B2

(12) United States Patent
Hashimoto et al.

(10) Patent No.: US 10,675,193 B2
(45) Date of Patent: Jun. 9, 2020

(54) WEARING ARTICLE

(71) Applicant: Unicharm Corporation, Shikokuchuo-shi, Ehime (JP)

(72) Inventors: Tatsuya Hashimoto, Kanonji (JP); Tetsuo Okubo, Kanonji (JP); Huanhuan Chen, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 559 days.

(21) Appl. No.: 15/322,167

(22) PCT Filed: Mar. 20, 2015

(86) PCT No.: PCT/JP2015/058463
§ 371 (c)(1),
(2) Date: Dec. 26, 2016

(87) PCT Pub. No.: WO2015/198663
PCT Pub. Date: Dec. 30, 2015

(65) Prior Publication Data
US 2017/0156945 A1 Jun. 8, 2017

(30) Foreign Application Priority Data

Jun. 27, 2014 (JP) .................................. 2014-133411

(51) Int. Cl.
*A61F 13/514* (2006.01)
*A61F 13/496* (2006.01)
(Continued)

(52) U.S. Cl.
CPC ........ *A61F 13/51496* (2013.01); *A61F 13/49* (2013.01); *A61F 13/496* (2013.01);
(Continued)

(58) Field of Classification Search
CPC .. A61F 13/49; A61F 13/496; A61F 13/51496; A61F 13/515; A61F 13/539;
(Continued)

(56) References Cited

U.S. PATENT DOCUMENTS 6,146,367 A * 11/2000 Otsubo ................... A61F 13/42
604/385.01
6,297,424 B1 * 10/2001 Olson ..................... A61F 13/42
604/361

(Continued)

FOREIGN PATENT DOCUMENTS

| JP | 2004-141640 A | 5/2004 |
| JP | 2004-188060 A | 7/2004 |
| JP | 2014-28308 A | 2/2014 |

OTHER PUBLICATIONS

International Search Report in PCT/JP2015/058463, dated Jun. 16, 2015.

*Primary Examiner* — Susan S Su
(74) *Attorney, Agent, or Firm* — Hauptman Ham, LLP

(57) ABSTRACT

The wearing article has front and rear waist regions and a crotch region wherein a first waist region as one of the front and rear waist regions includes an outer layer sheet located on non-skin-facing surface, an inner layer sheet located on the inner side compared to the outer layer sheet and an interlayer sheet interlaid between the inner and outer layer sheets and having a decorative element being visually recognizable from the non-skin-facing surface side of the outer layer sheet and the outer layer sheet is nonwoven fabrics formed from crimped conjugated fibers and a brightness value of the inner layer sheet is higher than a brightness value of the outer layer sheet.

7 Claims, 7 Drawing Sheets

(51) Int. Cl.
*A61F 13/49* (2006.01)
*A61F 13/84* (2006.01)
*A61F 13/515* (2006.01)
*A61F 13/539* (2006.01)

(52) U.S. Cl.
CPC .......... *A61F 13/514* (2013.01); *A61F 13/515* (2013.01); *A61F 13/539* (2013.01); *A61F 13/84* (2013.01); *A61F 2013/5395* (2013.01); *A61F 2013/8497* (2013.01)

(58) Field of Classification Search
CPC .............. A61F 13/84; A61F 2013/5395; A61F 2013/8497; A61F 13/49058–49061; A61F 2013/49063–49066; A61F 13/514–51405; A61F 2013/51407–51437; A61F 2013/51441; A61F 2013/51447; A61F 2013/51452
See application file for complete search history.

(56) References Cited

U.S. PATENT DOCUMENTS

| | | | |
|---|---|---|---|
| 6,365,795 B1* | 4/2002 | Suekane | A61F 13/84 604/367 |
| 6,468,630 B1* | 10/2002 | Mishima | A61F 13/4902 428/181 |
| 6,569,136 B1* | 5/2003 | Tao | A61F 13/5148 156/85 |
| 6,596,918 B1* | 7/2003 | Wehrle | A61F 13/42 604/361 |
| 6,719,742 B1* | 4/2004 | McCormack | A61F 13/51462 604/385.01 |
| 2002/0029025 A1* | 3/2002 | Furuya | A61F 13/51121 604/378 |
| 2004/0138633 A1* | 7/2004 | Mishima | A61F 13/42 604/361 |
| 2004/0167491 A1* | 8/2004 | Mizutani | A61F 13/15211 604/385.17 |
| 2005/0113774 A1* | 5/2005 | Ishikawa | A61F 13/49019 604/378 |
| 2005/0131374 A1* | 6/2005 | Otsubo | A61F 13/49011 604/385.27 |
| 2006/0020249 A1* | 1/2006 | Allen | A61F 13/42 604/361 |
| 2006/0161128 A1* | 7/2006 | Soga | A61F 13/49017 604/385.24 |
| 2008/0132872 A1 | 6/2008 | Trennepohl et al. | |
| 2008/0254263 A1* | 10/2008 | Yasui | A41D 31/02 428/172 |
| 2008/0294140 A1* | 11/2008 | Ecker | A61F 13/472 604/385.23 |
| 2009/0247979 A1* | 10/2009 | Sosalla | A61F 13/51478 604/385.01 |
| 2012/0165774 A1 | 6/2012 | Otsubo et al. | |
| 2012/0172825 A1* | 7/2012 | Ales | A61F 13/42 604/361 |
| 2014/0005621 A1* | 1/2014 | Roe | A61F 13/49004 604/365 |
| 2015/0250664 A1* | 9/2015 | Uda | A61F 13/4756 604/370 |

* cited by examiner

WEARING ARTICLE

RELATED APPLICATIONS

The present application is a National Phase of International Application Number PCT/JP2015/058463, filed Mar. 20, 2015, which claims priority to Japanese Application Number 2014-133411, filed Jun. 27, 2014.

TECHNICAL FIELD

The present invention relates to wearing articles such as disposable diaper, disposable toilet-training pant and disposable pant for incontinent persons.

BACKGROUND

Conventionally, wearing articles having a decorative element visually recognizable from outside is known. For example, Patent Literature 1 described below discloses a wearing article including, in a first waist region as one of front and rear waist regions, an outer layer sheet located on a non-skin-facing surface side, a printed sheet located on the interior surface of the outer layer sheet and printed with the decorative element visually recognizable from the outside of the outer layer sheet and an inner layer sheet located on the region of the inner surface of the outer layer sheet in which the printed sheet is not located. In the wearing article disclosed in this Patent Literature 1, the number of nonwoven fabric layers is minified in the region in which the printed sheet is located, in other words, the inner layer sheet is located only in the region in which the printed sheet is not located. Consequently, a mass per unit area in this region increases and the light transmittance in the region in which the printed sheet is located is higher than that in the region in which the printed sheet is not located.

CITATION LIST

Patent Literature

{PTL 1}: JP2004-141640 A

SUMMARY

Technical Problem

In the wearing article disclosed in {PTL 1}, a relatively high visibility for the decorative element is ensured by relatively enhancing the light transmittance in the region in which the printed sheet is located and a likelihood that the wearer's skin might be seen through the wearing article is restricted by keeping the light transmittance relatively low in the region in which the printed sheet is not located.

However, in this known wearing article, when it is tried to keep a thickness of the outer layer sheet relatively thin, thereby reducing a mass per unit area thereof in order to enhance the light transmittance in the region in which the printed sheet is located, there is a problem that a desired soft texture might be deteriorated. In addition, when it is tried to increase a mass per unit area of the inner layer sheet in order to improve the texture, there is another problem that the stiffness might be increased and the flexibility might be reduced.

In view of the problem set forth above, an object of the present invention is to provide a wearing article making it possible to enhance the visibility for the decorative element, to restrict the likelihood that wearer's skin might be seen through and to maintain flexibility and texture of the article.

Solution to Problem

The present invention is directed to a wearing article having a vertical direction, a lateral direction, a skin-facing surface and a non-skin-facing surface and including a first waist region as one of front and rear waist regions, a second waist region as the other thereof, a crotch region extending between the first and second waist regions and a liquid-absorbent core located at least in the crotch region of the first and second waist regions and the crotch region.

In the wearing article according to the present invention, the first waist region includes an outer layer sheet on the non-skin-facing surface, an inner layer sheet on the inner side compared to the outer layer sheet and an interlayer sheet interlaid between the inner and outer layer sheets and having a decorative element being visually recognizable from the non-skin-facing surface of the outer layer sheet, the outer layer sheet is nonwoven fabrics formed from crimped conjugated fibers and a brightness value of the inner layer sheet is higher than a brightness value of the outer layer sheet.

Advantageous Effects of Invention

In the wearing article according to one or more embodiments of the present invention, the first waist region includes the interlayer sheet located between the inner/outer layer sheets and having the decorative element adapted to be visually recognizable from the outside of the outer layer sheet. The brightness value of the inner layer sheet is higher than the brightness value of the outer layer sheet. Specifically, the interlayer sheet having the decorative element is located outside the inner layer sheet having a relatively high brightness value so that the decorative element may be visually recognized through the outer layer sheet having a relatively low brightness value and, in consequence, it is possible to enhance the visibility. In the region in which the interlayer sheet is not located, the inner layer sheet having a relatively high brightness value and the outer layer sheet are layered one upon another, thereby a likelihood that the wearer's skin might be seen through from the outside is restricted. Furthermore, the outer layer sheet is nonwoven fabrics formed of crimped conjugate fibers so that bulky and soft texture of the article may be maintained even when the fiber density is relatively low. In addition, the fiber density of the inner layer sheet may be kept relatively low to maintain the flexibility of the article.

BRIEF DESCRIPTION OF DRAWINGS

The drawings illustrate specific embodiments of the present invention including optional and preferred embodiments as well as essential features of the invention.

FIG. 7 (b) is a schematic sectional view taken along line VIIb-VIIb in FIG. 7 (a).

DESCRIPTION OF EMBODIMENTS

Figure 1:
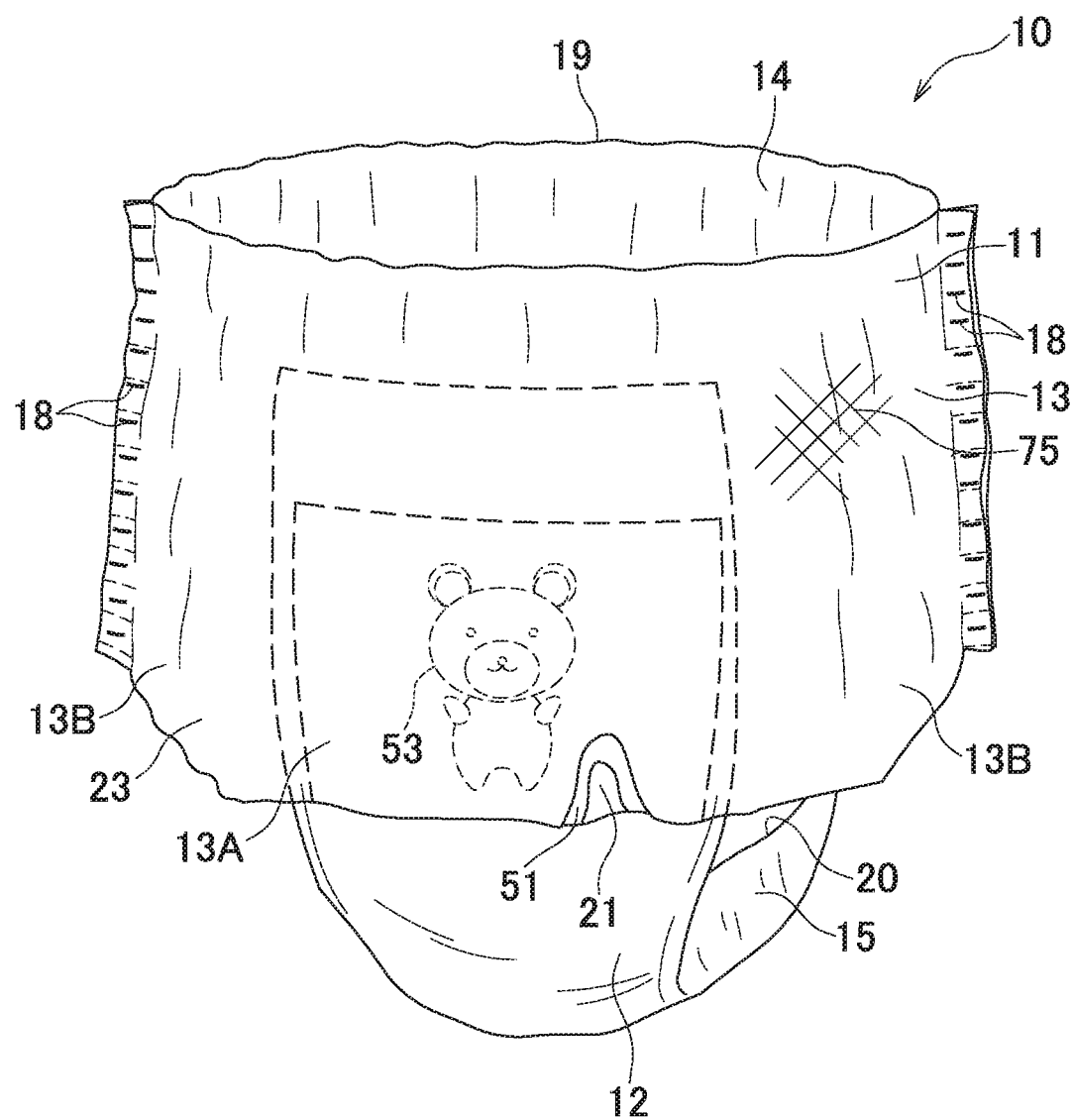
FIG. 1 is a partially cutaway perspective view of a diaper as an example of a wearing article according to the present invention as viewed from the front.

The embodiments described below relate to the wearing articles illustrated in FIGS. 1 through 7, including both optional and preferred features as well as those features which are essential features of the present invention. In FIGS. 3 through 6, respective elastic members described later in more detail are in a state stretched against a contractile force thereof to a degree that gathers are formed in sheet elements having respective elastic members attached thereon under the contractile force of these elastic members in a vertical direction Y and a lateral direction X may substantially disappear for a natural eyesight.

Referring to FIGS. 1 through 4, a disposable diaper 10 as an example of a wearing article according to the present invention has a vertical direction Y and a lateral direction X and includes a skin-facing surface, a non-skin-facing surface opposed to the former, an annular elastic waist panel 11 extending circumferentially about a wearer's waist, an absorbent chassis 12 attached to the elastic waist panel 11 and containing therein a liquid-absorbent core 43, a front waist region (first or second waist region) 13, a rear waist region (first or second waist region) 14 and a crotch region 15 lying between the front and rear waist regions 13, 14. The front and rear waist regions 13, 14 respectively have, as viewed in the lateral direction X, central regions 13A, 14A to be occupied by the liquid-absorbent core 43 and both lateral regions 13B, 14B defined outside the central regions 13A, 14A in the lateral direction X wherein interlayer sheets 51, 52 having decorative elements 53 are placed in the central regions 13A, 14A.

<Elastic Waist Panel>

The elastic waist panel 11 functions as an elastic belt and includes a front waist panel 16 defining the front waist region 13 and a rear waist panel 17 defining the rear waist region 14. The front and rear waist panels 16, 17 respectively have substantially trapezoidal shapes defined by inner end edges 16a, 17a, outer end edges 16b, 17b, outer side edges (both side edges of the front and rear waist regions) 16c, 17c extending inward from the outer end edges 16b, 17b and inner side edges 16d, 17d extending obliquely inward from the outer side edges 16c, 17c. Both outer side edges 16c of the front waist panel 16 and both outer side edges 17c of the rear waist panel 17 opposed to the former are overlapped and joined to each other alongside seams continually extending in the vertical direction Y by well-known means, for example, various kinds of heat-sealing means such as heat embossing/debossing or ultrasonic sealing so as to define a waist-opening 19 and a pair of leg-openings 20.

The front and rear waist panels 16, 17 respectively include inner layer sheets 21, 22 lying on the skin-facing surface, outer layer sheets 23, 24 lying on the non-skin-facing surface and interlayer sheets 51, 52 interlaid between the inner layer sheets 21, 22 and the outer layer sheets 23, 24, respectively.

The inner layer sheets 21, 22 respectively define contours of the front and rear waist panels 16, 17. As material for the inner layer sheets 21, 22, elastic fibrous nonwoven fabrics may be used, for example, well-known elastic fibrous nonwoven fabrics having a mass per unit area ranging from about 11 to about 30 g/m² such as spunbond fibrous nonwoven fabrics, meltblown fibrous nonwoven fabrics, heat-roll fibrous nonwoven fabrics, SMS (spunbond/meltblown/spunbond) fibrous nonwoven fabrics, air-laid fibrous nonwoven fabrics or air-through fibrous nonwoven fabrics may be used in isolation or in combination.

The outer layer sheets 23, 24 and the inner layer sheets 21, 22 are substantially the same in size and shape and respectively define contours of the front and rear waist panels 16, 17. As material for the outer layer sheets 23, 24, inelastic nonwoven fabrics having a mass per unit area ranging from about 20 to about 30 g/m² such as SMS fibrous nonwoven fabrics, spunbond fibrous nonwoven fabrics or air-through fibrous nonwoven fabrics may be used in isolation or in combination. In this regard, the outer layer sheets 23, 24 respectively have a total light transmittance at a level ensuring that respective decorative elements 53 on the interlayer sheets 51, 52 are visually recognized externally.

Specifically, when the outer layer sheets 23, 24 are formed of SMS fibrous nonwoven fabrics, spunbond fibrous nonwoven fabrics of air-through fibrous nonwoven fabrics each having a mass per unit area ranging from about 20 to about 30 g/m², the outer layer sheets 23, 24 respectively have the total light transmittance of 75% or higher, preferably 83% or higher. So long as the total light transmittance of the outer layer sheets 23, 24 is within such range, the decorative elements 53 on the respective outer layer sheets 23, 24 may be visually recognized from outside with no difficulty. The total light transmittance may be measured in conformity to JIS K 7375 using Color difference meter of flicker photometer type Z-300A manufactured by Nippon Denshoku Industries Co., Ltd.

The nonwoven fabrics used to form the outer layer sheets 23, 24 is composed of thermoplastic synthetic fibers in the form of conjugate fibers having crimps. Fineness of the conjugate fibers preferably ranges from about 1.0 to about 8.0 dtex and is about 1.4 dtex in the present embodiment. For the conjugate fibers, core-in-sheath type or side-by-side type conjugate fibers formed from two or more types of raw materials respectively having melting points different from each other, for example, polypropylene and polyethylene may be used. As such conjugate fibers 91, at least the fibers having crimps expressed in production of the outer layer sheets 23 24, for example, under heating, or the fibers having crimps actualized by machine process or heat treatment may be used, wherein the number of crimps preferably ranges from 15 to 25 per 25 mm.

The inner layer sheets 21, 22 have respectively a brightness higher than that of the respective outer layer sheets 23, 24. Specifically, a content of titanium oxide in the respective inner layer sheets 21, 22 is a 0.1 mass % or more and the brightness thereof ranges from 45 to 55. Meanwhile, a content of titanium oxide in the respective outer layer sheets 23, 24 is 0.1 mass % or less, preferably 0.0 mass % or and the brightness ranges from 40 to 50.

Figure 4:
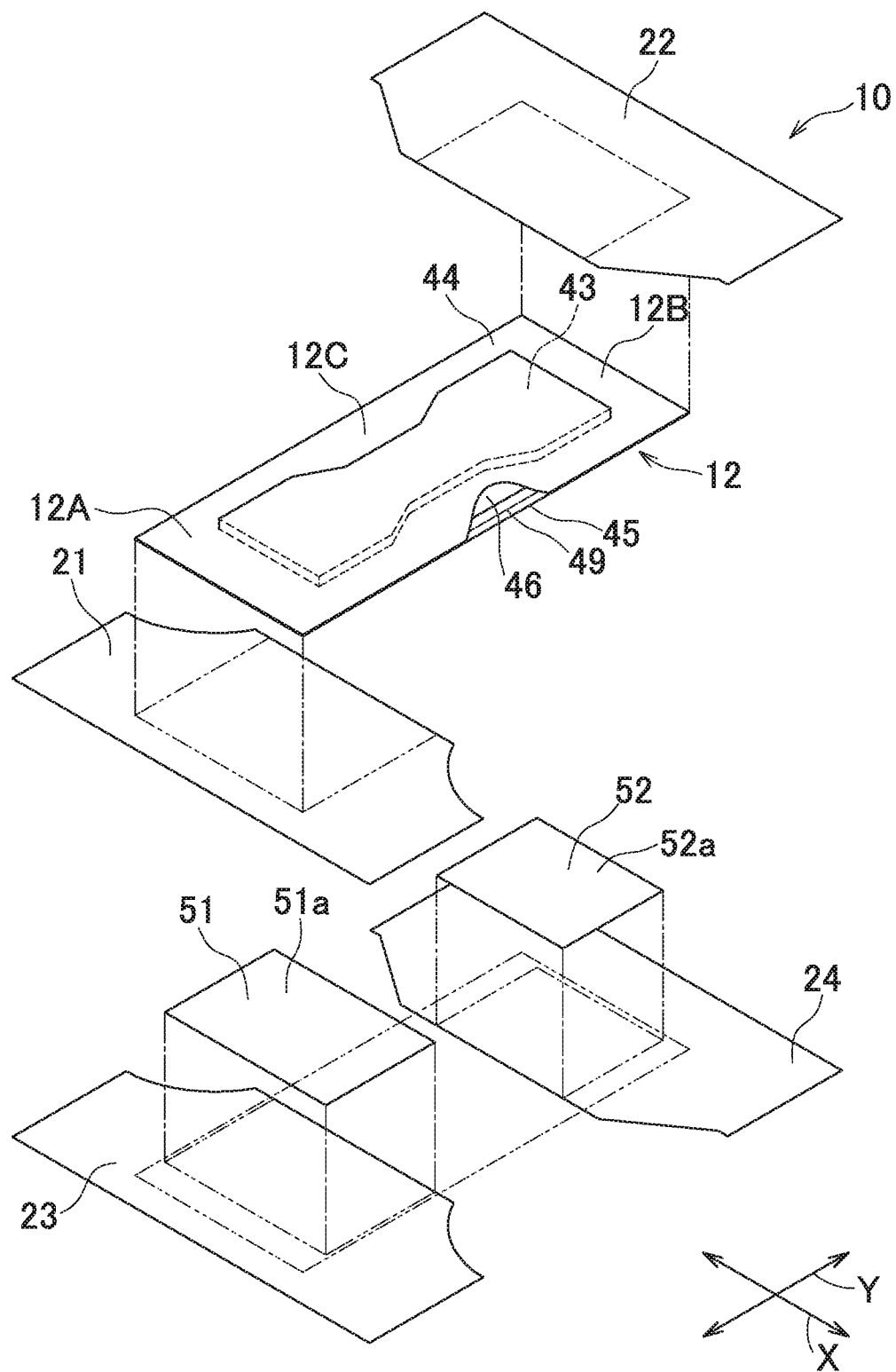
FIG. 4 is a partially cutaway exploded perspective view of the diaper.
Figure 5:
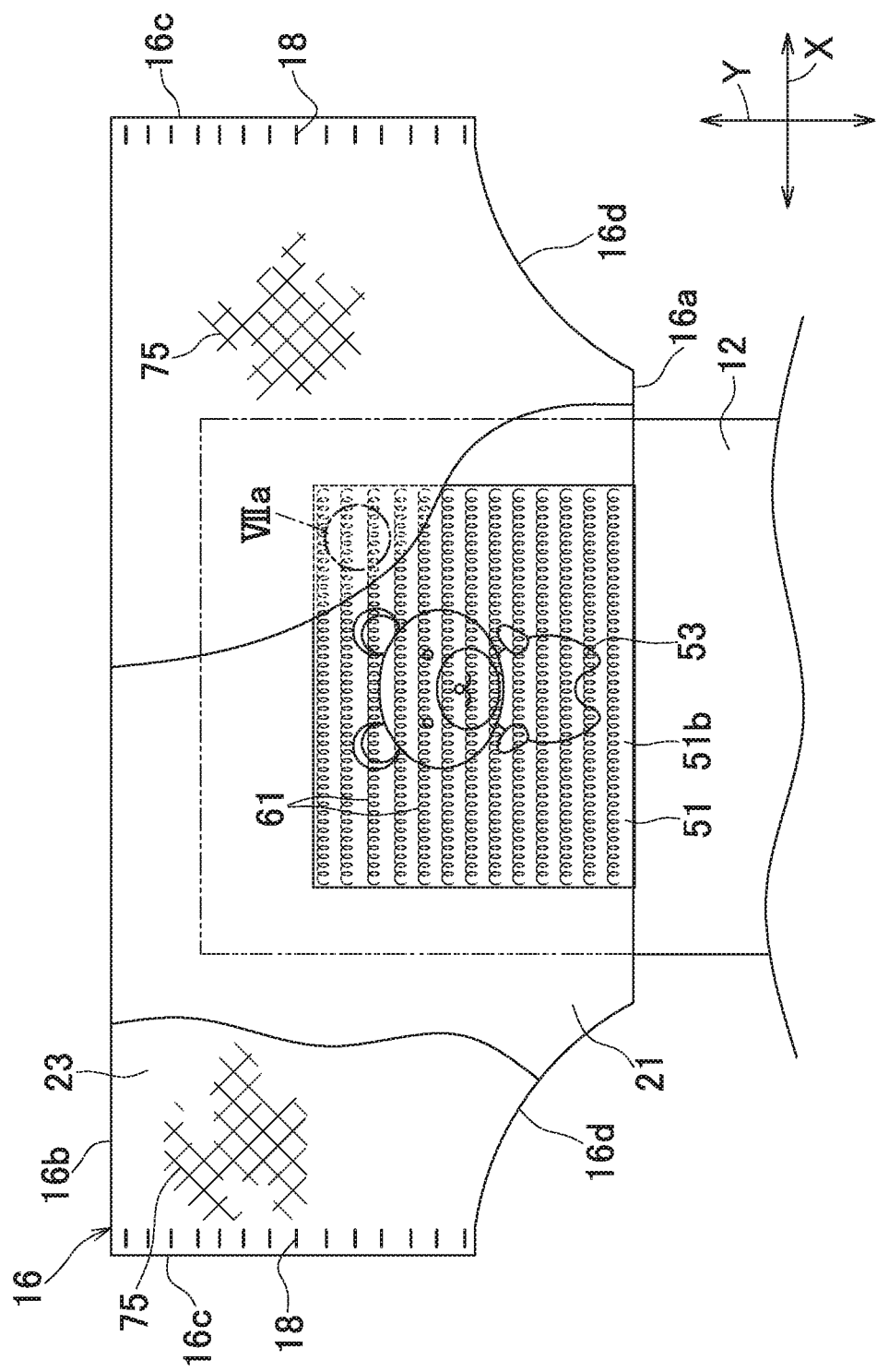
FIG. 5 is a partially cutaway plan view of a front waist panel as viewed from the side of non-skin-facing surface.
Figure 6:
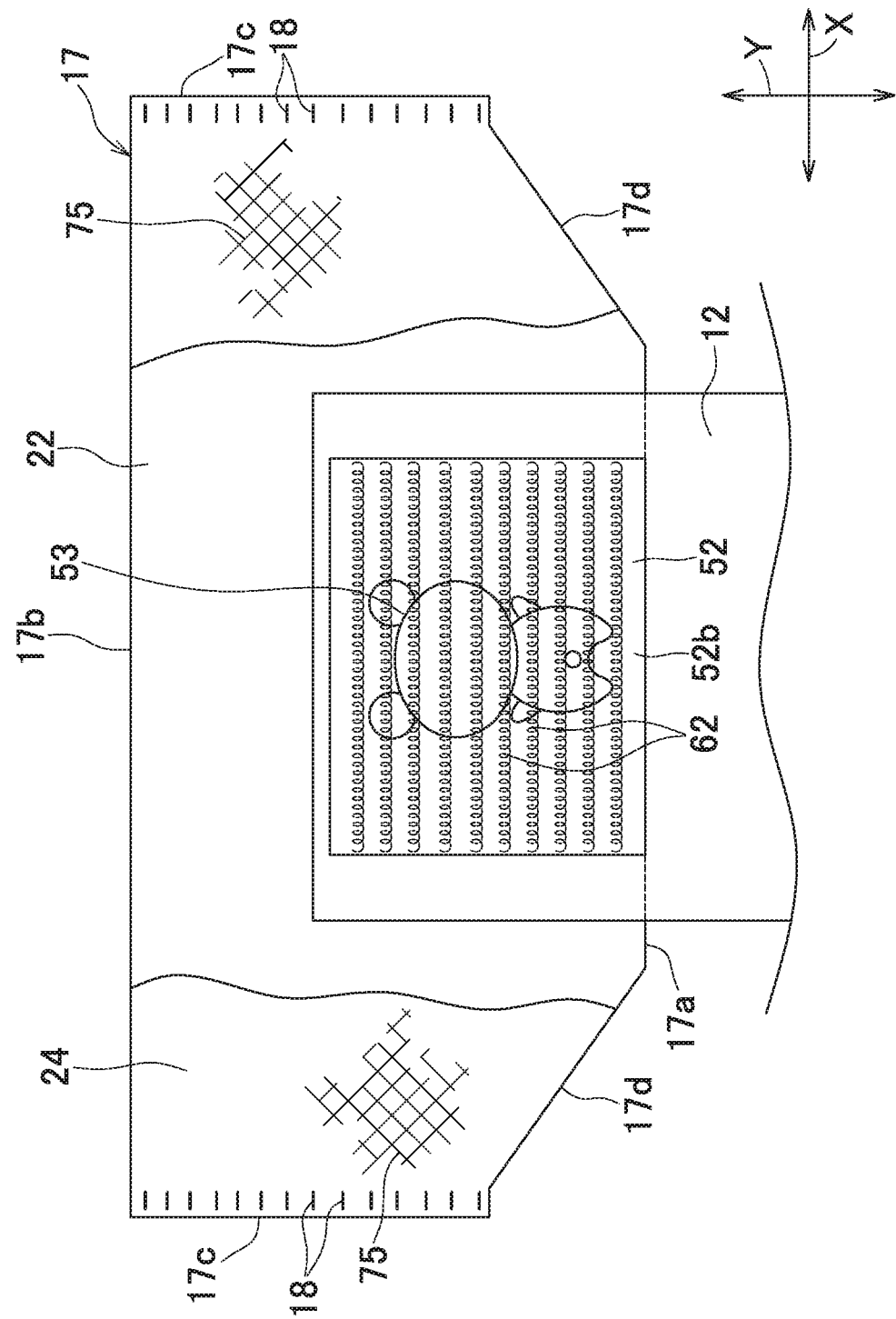
FIG. 6 is a partially cutaway exploded plan view of a rear waist panel as viewed from the side of non-skin-facing surface.

Between the inner layer sheets 21, 22 and the outer layer sheets 23, 24, the interlayer sheets 51, 52 printed with the decorative elements 53 which are visually recognizable externally of the diaper 10 (i.e., externally of the outer layer sheets 23, 24) are interlaid. Referring to FIGS. 4 through 6, the interlayer sheets 51, 52 have generally rectangular defined by first surfaces 51a, 52a facing the inner layer sheets 21, 22 and second surfaces 51b, 52b facing the outer layer sheets 23, 24 wherein these interlayer sheets 51, 52 are formed of liquid-impermeable fibrous nonwoven fabrics, liquid-impermeable but breathable plastic films or a laminated sheet thereof. While a graphic of animal character is exemplarily illustrated as the decorative elements 53 for the present embodiment, various well-known decorative elements in the forms of, for example, diagrams, decorative patterns, graphics, letters, symbols or colorations may be adopted so long as these decorative elements are visually recognizable and configurations thereof are apprehensible from the outside.

The second surfaces 51b, 52b of the interlayer sheets 51, 52 are bonded to the respective interior surfaces of the outer layer sheets 23, 24 by well-known bonding means 61, 62 such as hot melt adhesives. In the front waist region 13, the first surface 51a of the interlayer sheet 51 is bonded to the exterior surface of the inner layer sheet 21 by well-known bonding means such as hot melt adhesives and, in the rear waist region 14, the first surface 52a of the interlayer sheet 52 is bonded to the exterior surface of the absorbent chassis 12 by well-known bonding means such as hot melt adhesives.

Over a range having neither the interlayer sheet 51 nor the interlayer sheet 52 located therein, the inner and outer layer sheets 21 through 24 are bonded to each other by well-known bonding means such as hot melt adhesives. The front and rear waist panels 16, 17 are elasticized in the lateral direction X almost over the entire area thereof under the influence of the inner layer sheets 21, 22 having elasticity.

<Absorbent Chassis)

Figure 2:
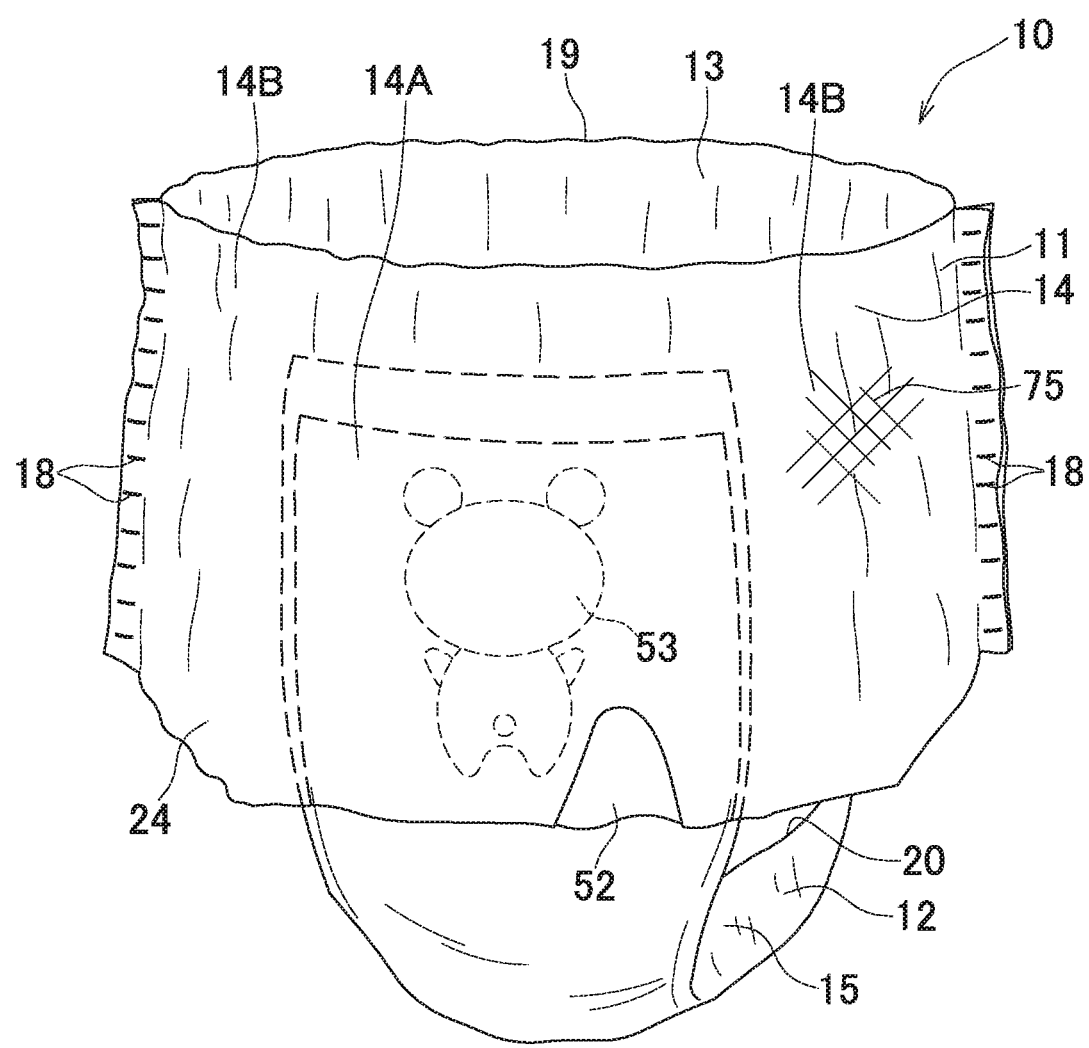
FIG. 2 is a partially cutaway perspective view of a diaper put on a wearer's body as viewed from the rear side.
Figure 3:
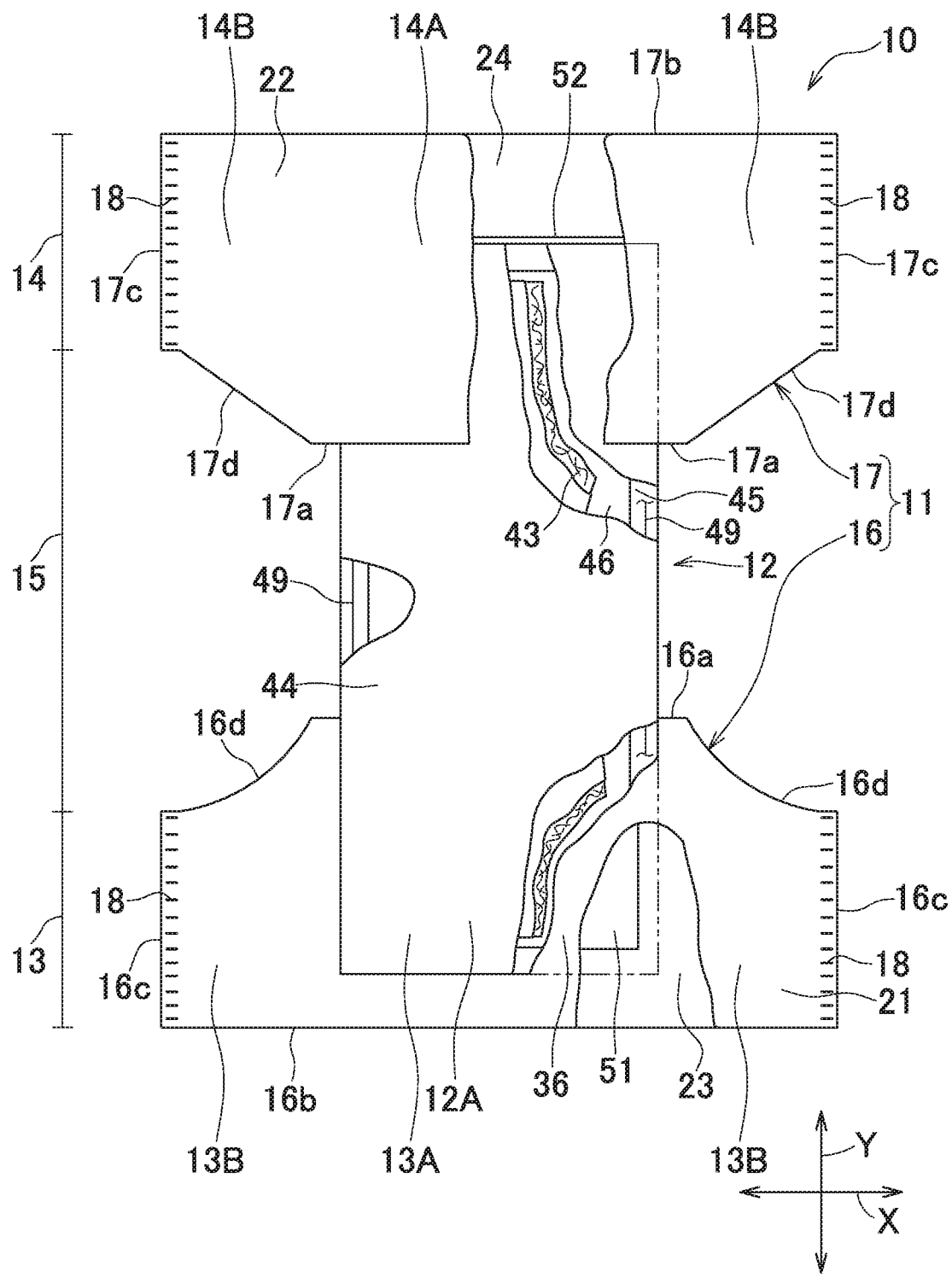
FIG. 3 is a partially cutaway developed plan view of the diaper.

Referring to FIGS. 2 and 3, the absorbent chassis 12 is defined by front and rear end portions 12A, 12B attached to the front and rear waist panels 16, 17, respectively, and an intermediate portion 12C extending between the front and rear portions 12A, 12B and includes the liquid-absorbent core 43 extending in the vertical direction Y at least in the crotch region 15, a topsheet 44 formed of hydrophilic fibrous nonwoven fabrics lying on the skin-facing surface of the liquid-absorbent core 43, a backsheet 45 formed of hydrophobic or hardly-liquid-permeable fibrous nonwoven fabrics lying on the non-skin-facing surface of the liquid-absorbent core 43 and a liquid-impermeable leakage-barrier sheet 46 interlaid between the liquid-absorbent core 43 and the backsheet 45 wherein the leakage-barrier sheet 46 has a size sufficient to cover at least the entire surface of the liquid-absorbent core 43 facing the backsheet 45. As material for the top- and backsheets 44, 45, various well-known fibrous nonwoven fabrics such as SMS fibrous nonwoven fabrics and spunbond nonwoven fabrics may be used.

The front end portion 12A of the absorbent chassis 12 is fixed to the interior surface of the front waist panel 16 (i.e., the interior surface of the inner layer sheet 21) through the front bonding region distributed with bonding means such as hot melt adhesive and the rear end portion 12B is interlaid between the interlayer sheet 52 and the inner layer sheet 22 of the rear waist panel 17 and fixed therebetween through the rear bonding region distributed with bonding means such as hot melt adhesive.

The liquid-absorbent core 43 is a mixture of a required quantity of superabsorbent polymer particles and a required quantity of wood fluff pulp and is semi-rigidity higher than the sheet elements constituting the diaper 10. The liquid-absorbent core 43 has a panel geometry having a central portion in the vertical direction Y narrower than the other portion and the entirety of the liquid-absorbent core 43 is wrapped by a liquid-diffusive sheet. The topsheet 44 and the backsheet 45 extend outward from a periphery of the liquid-absorbent core 43 and these portions of the top- and backsheets 44, 45 extending outward bonded to each other by hot melt adhesive (not shown) so as to form a pair of side flaps extending outward in the lateral direction X from both side edges of the liquid-absorbent core 43 and a pair of end flaps extending outward in the vertical direction Y from both end edges of the liquid-absorbent core 43. Leg elastic members 49 extending in the vertical direction Y are contractibly secured under tension to the respective side flaps.

As has previously been described, in the front and rear waist regions 13, 14 of the diaper 10, the interlayer sheets 51, 52 are interlaid between the inner and outer layer sheets 21 through 24 and bonded to the non-skin-facing surfaces of the outer layer sheets 23, 24, respectively, wherein the brightness of the inner layer sheets 21, 22 are higher than that of the outer layer sheets 23, 24 so that the decorative elements 53 may be visually recognized through the outer layer sheets 23, 24 of which the brightness is relatively low and a visibility for the decorative elements 53 may be correspondingly improved. To ensure such effect, preferably the content of titanium oxide in the outer layer sheets 23, 24 is about 0.1 mass % or less and the content of titanium oxide in the inner sheets 21, 22 is about 0.1 mass % or higher. Furthermore, in both lateral regions 13B, 14B of the front and rear waist regions 13, 14 in which none of the interlayer sheets 51, 52 are located, the outer layer sheets 23, 24 are layered with the inner layer sheets 21, 22 having the relatively high brightness to restrict a likelihood that the wearer's skin might be seen through. The brightness in both lateral regions 13B, 14B is preferably higher than 55 and, by setting the brightness to such value, it is possible to restrict more reliably the likelihood that the wearer's skin might be seen through. In addition, the brightness on both lateral regions 13B, 14B is preferably ranging from 55 to 70.

Figure 7:
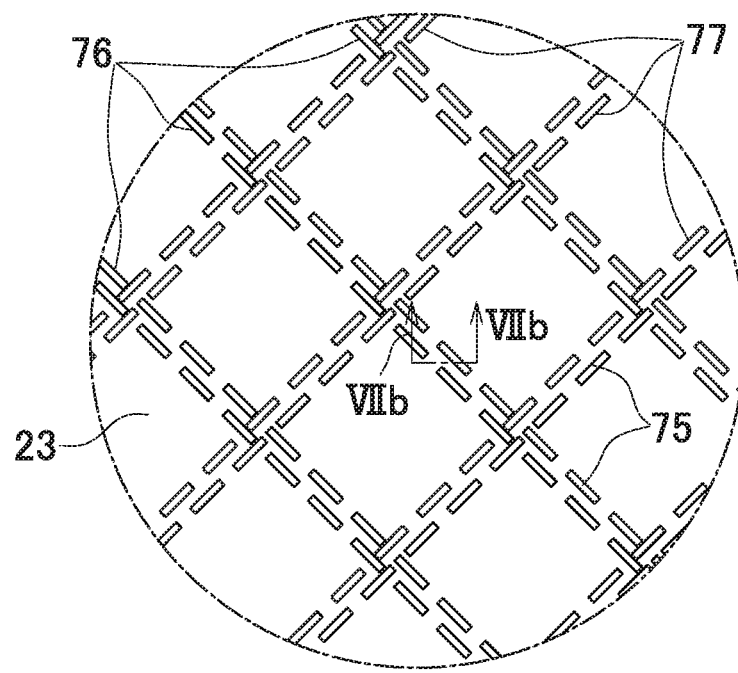
FIG. 7 (a) is a scale-enlarged diagram of a region VIIa in FIG. 5.
Figure 7:
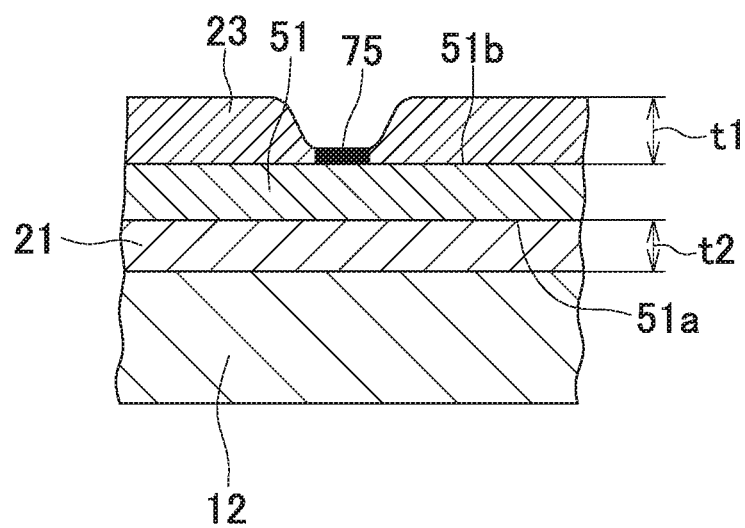

FIG. 7 (a) is a scale-enlarged diagram of a region VIIa in FIG. 5 (i.e., part of the central zone 13A of the front waist region 13) and FIG. 7 (b) is a schematic sectional view taken along line VIIb-VIIb in FIG. 7 (a). While FIG. 7 illustrates only the front waist region 13 and not the rear waist region 14, a relationship between, except the absorbent chassis 12, the inner and outer layer sheets 21 through 24 and the interlayer sheets 51, 52 is the same to such relationship in the front waist region 13. In view of this, a correlation of the respective sheets 21 through 24, 51, 52 in the front and rear waist regions 13, 14 will be described hereunder in reference to FIG. 7.

Referring to FIG. 7 (a), the outer layer sheets 23, 24 are subjected to a thermocompression bonding by embossing/debossing from the non-skin-facing surface toward the skin-facing surface so as to form a plurality of heat-sealed regions 75 over the entire surface. In the heat-sealed region 75, the conjugate fibers are thermal fusion bonded to each other and formed into film. A plurality of such heat-sealed regions are linearly arranged to form a plurality of first heat-sealed lines 76 extending in a first direction intersecting with the vertical direction Y and the lateral direction X and a plurality of second heat-sealed lines 77 extending in a second direction intersecting with the vertical direction Y, the lateral direction X and the first direction. The first heat-sealed line 76 is defined by a plurality of the heat-sealed regions 75 arranged in two rows extending in the first direction and the second heat-sealed line 77 is defined by a plurality of the heat-sealed regions 75 arranged in two rows extending in the second direction.

In the portions of the outer layer sheets 23, 24 respectively facing the second surfaces 51b, 52b of the interlayer sheets 51, 52, an area of the heat-sealed regions 75 is preferably ranging from about 4% to about 8% of a total area of the portions facing the second surfaces 51b, 52b. Referring to FIG. 7 (b), the sheets are formed into film so that the sheets may be thinned thereby a visibility for the decorative elements 53 may be improved and a stiffness may be enhanced. By ranging the area of the heat-sealed regions 75 in the portions facing the second surfaces 51b, 52b in this manner, it is possible to maintain a flexibility of the outer layer sheets 23, 24 and it is possible to improve the visibility for the decorative elements 53. Meanwhile, it is possible to arrange so that the area percentage of the heat-sealed regions 75 in the portions of the outer layer sheets 23, 24 facing the interlayer sheets 51, 52 may be higher than the area percentage of the heat-sealed regions 75 in the non-facing portion (i.e., the regions in which none of the interlayer sheets 51, 52 are located). Such arrangement makes it possible to improve the visibility for the decorative elements 53 in the facing portions and it is possible to improve the flexibility in the non-facing portion. The outer layer sheets 23, 24 are formed of crimped conjugate fibers and more bulky than such outer layer sheets formed of fibers having no crimps so long as the mass per unit area is the same and there is a likelihood that the visibility might be deteriorated. However, the formation of the heat-sealed regions 75 makes it possible to ensure the high visibility.

In the diaper 10 according to the present embodiment, the outer layer sheets 23, 24 are the nonwoven fabrics composed of crimped conjugate fibers making it possible to maintain a bulky and flexible texture even if the mass per unit area is relatively low. For this reason, a mass per unit area of the inner layer sheets 21, 22 may be kept relatively low to maintain a desired flexibility. To assure such advantageous effect, the outer layer sheets 23, 24 preferably have a mass per unit area ranging from 20 to 30 g/m$^2$, a fineness ranging from 1.0 to 8.0 dtex and a thickness dimension t1 ranging from 0.15 to 1.5 mm. The inner layer sheets 21, 22 preferably have a mass per unit area ranging from 11 to 30 g/m$^2$, a fineness ranging from 1.0 to 8.0 dtex and a thickness dimension t2 ranges from 0.05 to 1.0 mm. In addition, the dimension t1 of the outer layer sheets 23, 24 is preferably larger than the dimension t1 of the inner layer sheets 21, 22. Such dimensional terms that the thickness dimension t2 of the inner layer sheets 21, 22 is smaller than the thickness dimension t1 of the outer layer sheets 23, 24 makes it possible to improve the visibility for the decorative elements 53, to restrict the stiffness in the front and rear waist regions 13, 14, thereby improving the flexibility of these regions. The expression "the thickness dimension t1 of the outer layer sheets 23, 24" means the thickness dimension in the non-heat-sealed regions (i.e., the region in which none of the heat-sealed regions 75 is formed) of the outer layer sheets 23, 24. The expression "the thickness dimension of the inner layer sheets 21, 22" means the thickness dimension of the inner layer sheets 21, 22 under tension as illustrated in FIG. 2. As an additional advantageous effect, by using elastically stretchable/contractible sheets as the inner layer sheets 21, 22, it is possible to restrict the stiffness, thereby improving the flexibility compared to string- or strand-type elastic elements attached to inelastic sheet elements to elasticize these sheet elements.

Referring to FIGS. 5 and 6, in the front and rear waist regions 13, 14, as has previously been described, the interlayer sheets 51, 52 are bonded to the interior surfaces of the outer layer sheets 23, 24 by the bonding means 61, 62 evenly distributed to the entire areas of the second surfaces 51b, 52b so as to define a given pattern. While the bonding means 61, 62 are distributed to the second surfaces 51b, 52b in the spiral pattern according to the present embodiment, the pattern of the bonding means 61, 62 is not limited to the spiral pattern and it is also possible to use the other pattern, for example, dot- or Q-pattern. A mass per unit area of the bonding means 61, 62 ranges from about 2.0 to about 7.0 g/m$^2$. In the second surfaces 51b, 52b of the interlayer sheets 51, 52, the area distributed with the bonding means 61, 62 is preferably about 4% or more of the entire area of the second surfaces 51b, 52b and more preferably ranges from about 4 to about 6% of the entire area of the second 51b, 52b. By distributing the bonding means 61, 62 to the second surfaces 51b, 52b over about 4% or more of the total area of the second surfaces 51b, 52b, it is possible to ensure a relatively large area in which the interlayer sheets 51, 52 are closely attached to the outer layer sheets 23, 24, thereby improving the visibility. In addition, by ranging the distribution area between about 4 to about 6%, it is also possible to improve the flexibility.

In addition, by limiting the content of titanium oxide in the outer layer sheets 23, 24 to about 0.1 mass % or less, it is possible to attach the interlayer sheets 51, 52 and the outer layer sheets 23, 24 further closely to each other and, in consequence, it is possible to improve the visibility for the decorative elements 53. It is for the reason that, when a content of titanium oxide is at a relatively high level, there is a likelihood that the surfaces of the fibrous nonwoven fabrics respectively defining the outer layer sheets 23, 24 might become irregular and deteriorate a degree of adhesion between the outer layer sheets 23, 24 and the interlayer sheets 51, 52. Meanwhile, in the diaper 10 according to the present embodiment, by limiting the content of titanium oxide to about 0.1 mass % or less, it is possible to smooth the surfaces of the respective nonwoven fabrics and thereby to improve the degree of adhesion between the outer layer sheets 23, 24 and the interlayer sheets 51, 52.

<Measuring Method for Brightness>

Following the procedure as described below, brightness of the respective sheets 21 through 24 was measured by use of MODEL ZE 2000 manufactured by Nippon Denshoku Industries Co., Ltd. From the respective sheets 21 through 24, square-shaped test pieces each having dimension of 50 mm in the lateral direction X and the vertical direction Y were cut out. After a testing device had been powered up and left unattended for 15 minutes, the respective test pieces were standardized in the test device with use of a standard plate defined by X=93.06, Y=95.09 and Z=112.00, then the respective test pieces were placed on a reflective specimen carrier, chucked by black frame and measurement of brightness was conducted on the respective test pieces. Five test pieces were prepared for the respective sheets 21 through 24 and an average value of respective five test pieces was obtained as the brightness values for the respective sheets 21 through 24. The test pieces of the inner layer sheets 21, 22 were cut out from these sheets under tension as illustrated in FIG. 2 and the brightness values of these sheets 21, 22 were measured on the test pieces under tension.

The constituent elements of the disposable diaper 10 are not limited to those described in the specification but the other various types of materials widely used in the relevant technical field may be used without limitation unless otherwise stated. The terms "first" and "second" used in the specification and Claims of this invention are used merely to distinguish the similar elements, similar positions or the other similar items.

The disclosure relating to the present invention described above may be arranged at least as follows.

A diaper (wearing article) 10 having a vertical direction Y, a lateral direction X, skin-facing surface and non-skin-facing surface and including a first waist region 13 as one of front and rear waist regions 13, 14, a second waist region 14 as the other thereof, a crotch region 15 extending between the first and second waist regions 13, 14 and a liquid-absorbent core 43 located at least in the crotch region 15 within a range defined by the first and second waist regions 13, 14 and the crotch region 15, wherein: the first waist region 13 includes an outer layer sheet 23 on the non-skin-facing surface, an inner layer sheet 21 on the inner side compared to the outer layer sheet 23 and an interlayer sheet 51 interlaid between the inner and outer layer sheets 21, 23 and having a decorative element being visually recognizable from the non-skin-facing surface of the outer layer sheet 23; the outer layer sheet 23 is nonwoven fabrics formed from crimped conjugated fibers; and a brightness value of the inner layer sheet 21 is higher than a brightness value of the outer layer sheet 23.

The present invention disclosed in the paragraph {0036} may include embodiments at least as described below and these embodiments may be taken in isolation or in combination.

(1) The first waist region 13 has a central region 13A in which the liquid-absorbent core 43 is located and both lateral regions 13B defined outside the central region 13A as viewed in the lateral direction X; and the brightness value of the lateral regions 13B is 55 or higher.

(2) The outer layer sheet 23 has a mass per unit area ranging from 20 to 30 g/m², a fineness ranging from 1.0 to 8.0 dtex, a thickness dimension ranging from 0.15 to 1.5 mm, and a brightness value ranging from 40 to 50.

(3) The outer layer sheet 23 is not elastically tensile and the inner layer sheet 21 being elastically tensile is attached under tension to the outer layer sheet 23.

(4) The outer layer sheet 23 and the interlayer sheet 51 are bonded to each other by bonding means 61 evenly distributed to the interlayer sheet 51 over an entire area thereof so that the area distributed with the bonding means 61 may be 4% or more of the whole area of the interlayer sheet 51.

(5) The outer layer sheet 23 has heat-sealed regions 75 in which the conjugate fibers are heat-sealed to each other by thermocompression bonding.

(6) A content of titanium oxide in the outer layer sheet 23 is 0.1 mass % or less.

The invention claimed is:

1. A wearing article having a vertical direction, a lateral direction, a skin-facing surface and a non-skin-facing surface and including a first waist region as one of front and rear waist regions, a second waist region as the other thereof, a crotch region extending between the first and second waist regions and a liquid-absorbent core located at least in the crotch region within a range defined by the first and second waist regions and the crotch region, wherein:

the first waist region includes an outer layer sheet on the non-skin-facing surface, an inner layer sheet on the inner side compared to the outer layer sheet and an interlayer sheet interlaid between the inner and outer layer sheets and having a decorative element being visually recognizable from the non-skin-facing surface side of the outer layer sheet;

the outer layer sheet is nonwoven fabrics formed from crimped conjugated fibers; and a brightness value of the inner layer sheet is higher than a brightness value of the outer layer sheet.

2. The wearing article according to claim 1, wherein:

the first waist region has a central region in which the liquid-absorbent core is located and both lateral regions defined outside the central region as viewed in the lateral direction; and the brightness value of the lateral regions is 55 or higher.

3. The wearing article according to claim 1, wherein the outer layer sheet has a mass per unit area ranging from 20 to 30 g/m², a fineness ranging from 1.0 to 8.0 dtex, a thickness dimension ranging from 0.15 to 1.5 mm, and a brightness value ranging from 40 to 50.

4. The wearing article according claim 1, wherein the outer layer sheet is not elastically tensile and the inner layer sheet being elastically tensile is attached to the outer layer sheet under tension.

5. The wearing article according to claim 1, wherein the outer layer sheet and the interlayer sheet are bonded to each other by bonding means evenly distributed to the interlayer sheet over an entire area thereof so that the area distributed with the bonding means may be 4% or more of the whole area of the interlayer sheet.

6. The wearing article according to claim 1, wherein the outer layer sheet has heat-sealed regions in which the conjugate fibers are heat-sealed to each other by thermocompression bonding.

7. The wearing article according to claim 1, wherein a content of titanium oxide in the outer layer sheet is 0.1 mass % or less.

* * * * *